United States Patent [19]

Calton

[11] 4,228,079
[45] Oct. 14, 1980

[54] DIALKOXY MONORDEN DERIVATIVES

[75] Inventor: Gary J. Calton, Elkridge, Md.

[73] Assignee: W. R. Grace & Co., New York, N.Y.

[21] Appl. No.: 955,705

[22] Filed: Oct. 30, 1978

Related U.S. Application Data

[63] Continuation-in-part of Ser. No. 874,348, Feb. 1, 1978, abandoned.

[51] Int. Cl.$^2$ ............................................. C07D 493/04
[52] U.S. Cl. ................................ 260/343.41; 424/279
[58] Field of Search .................................... 260/343.41

[56] References Cited

U.S. PATENT DOCUMENTS

| | | | |
|---|---|---|---|
| 3,373,038 | 3/1968 | Hodge et al. .................. | 260/343.41 |
| 3,428,526 | 2/1969 | Sigg et al. ........................ | 195/80 R |

OTHER PUBLICATIONS

Mirrington et al. Tetrahedron Letters, No. 7, pp. 365-370, 1964.
McCapra et al. Tetrahedron Letters, No. 15, pp. 869-875, 1964.
Evans Chem. Abst. vol. 66, 1967.

*Primary Examiner*—Henry R. Jiles
*Assistant Examiner*—Jane T. Fan
*Attorney, Agent, or Firm*—Philip M. Pippenger

[57] ABSTRACT

Disclosed herein are novel dialkoxy derivatives of monorden corresponding to the structural formula:

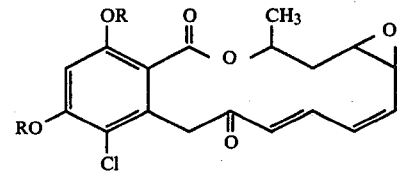

wherein R is an alkyl group having from 2 to 8 carbon atoms, the two R groups being the same or different. The novel compounds of the invention are useful as nematocides.

3 Claims, No Drawings

DIALKOXY MONORDEN DERIVATIVES

CROSS-REFERENCE TO RELATED APPLICATIONS

This application is a continuation-in-part of application Ser. No. 874,348, filed Feb. 1, 1978 of G. J. Calton, entitled "Dialkoxy Monorden Derivatives". This application is now abandoned. This application is also related to application Ser. No. 874,207, filed Feb. 1, 1978 of G. J. Calton and M. A. Espenshade entitled "Production of Monorden".

BACKGROUND OF THE INVENTION

U.S. Pat. No. 3,428,526 describes the production of monorden and states that monorden possesses a strong inhibiting effect on the increase of tumor cells of the mouse Mastocytoma p. 815 in vitro. Preparation of monorden is also described by McCapra et al, Tetrahedron Letters, 869–875 (1964) and by Mirrington et al (Tetrahedron Letters, 365–370 (1964)). Mirrington et al also describes the conversion of monorden to dimethoxy monorden by reaction with potassium carbonate/methyl iodide.

DESCRIPTION OF THE INVENTION

The invention is novel derivatives of dialkoxy monorden corresponding to the structural formula:

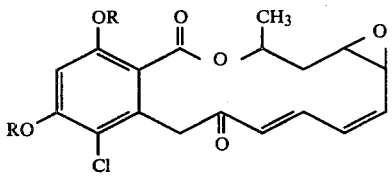

wherein R is an alkyl group having from 2 to 8 carbon atoms, the two R groups being the same or different. Because of the method of synthesis, the R groups are usually identical. The R groups can be either straight-chain or branched and preferably have from 2 to 4 carbon atoms. Examples of compounds of the invention include diethoxy monorden, dipropoxy monorden, diisopropoxy monorden, dibutoxy monorden, diisobutoxy monorden and dioctoxy monorden.

The scientific name for monorden is 5-chloro-6-(7,8-epoxy-10-hydroxy-2-oxo-3,5-undecyldienyl)-β-resorcylic acid μ-lactone. Monorden is also designated in the literature as radicicol and Rhi 12-648. Accordingly, the compounds of the invention can alternatively be designated as radicicol derivatives or the nomenclature can be based on the lengthy scientific designation.

The preparation of monorden is described in the references cited above. Using monorden as the starting material, the dialkoxy derivatives of the present invention are prepared by Williamson synthesis, using a method similar to that described by Mirrington et al for the preparation of the dimethoxy derivatives. Specifically, the derivatives of the invention are prepared by reacting monorden with potassium carbonate/alkyl iodide in an organic material which is a solvent for the reactants as well as being non-reactive therewith. Generally, the molar ratio of monorden to alkyl iodide is from about 1 to about 1.5. Suitable solvents include acetone and other ketones such as heptanone, hexanone and methyl ethyl ketone. Solvents such as alcohols or acids are not employed because of the possibility that they may be reactive. Ethers (e.g. diethyl ether, dioxane) may also be employed. The reaction is generally carried out at from about 30 to 120° C. and for from about 2 to about 10 hours. As would be apparent to one of ordinary skill in chemical synthesis, the variables such as time, temperature, pressure, ratios of reactants, solvents, etc., can be varied to maximize yields. It is not believed that any of the preceding variables are critical in the sense that a certain precise value must be present to obtain a reaction. Generally, it is believed that reaction conditions approximating the ranges specified above are sufficient. Using an alkyl iodide as described, the progress of the reaction can be monitored colorimetrically if desired.

Following reaction, the reaction mixture is processed and the dialkoxy derivative isolated by conventional techniques. For example, the solvent (e.g., acetone) is removed by distillation and the dry residue is taken up in a less polar solvent (e.g. chloroform) thereby removing residual $K_2CO_3$. The volume of the chloroform solution is reduced to an amount easily handled (e.g. about 25 mg of product per ml.) and the resulting solution is chromatographed on an appropriate substrate, e.g. silica or alumina. The derivative can be eluted with chloroform or mixtures of chloroform/hexane. As would be apparent, the eluant should be monitored to isolate the fraction in which the maximum yield of the dialkoxy derivative is obtained.

Monorden derivatives produced as described have been found to inhibit the growth of cancerous human nasopharynx (KB) cells in vitro. This is a recognized test for antitumor activity, e.g. see *Cancer Chem. Rpts.*, 25, 52 (1962). The monorden derivatives have also exhibited activity against mouse lymphocytic leukemia cells in vitro (P 388). This, too, is a recognized test for antitumor activity, e.g., see National Cancer Institute protocol, Drug Screening Section.

EXAMPLE 1—SYNTHESIS OF DIETHOXY MONORDEN

Monorden (200 mg.-0.0055 moles) was dissolved in 8.3 ml. of dry acetone (distilled from potassium carbonate). To this mixture was added 0.7746 gm. (0.0055 M.) of anhydrous potassium carbonate and 0.652 ml. (0.0082 M.) of ethyliodide. The mixture was then refluxed on a water bath at 56° for six hours. The acetone solubles were pipetted off and dried to yield 357.2 mg. The dried material was extracted with chloroform to eliminate potassium carbonate. The chloroform solubles amounted to 199.6 mg. Thin layer chromatograms of the extract were run in chloroform/methanol 9:1, methanol and chloroform. It was found that the best separation was achieved in chloroform. Impure diethoxy monorden (199.6 mg.) was then inoculated on a 134 cc. silica gel column and eluted with chloroform. Diethoxy monorden was eluted as the principal component and was recrystallized from methanol to yield fine, light yellow, needle-shaped crystals.

The yellow crystals, identified as diethoxy monorden, had the characteristics set forth in Table I.

EXAMPLE II—SYNTHESIS OF DI-N-PROPOXY MONORDEN

Similar to Example I, dipropoxy monorden was prepared by dissolving 200 mg. of monorden (0.0055 mole) in 8.3 ml. of dry acetone. To this mixture was added 774.6 mg. (0.0055 mole) of anhydrous potassium carbonate followed by 0.796 ml. (0.0082 mole) of 1-iodopropane. The mixture was refluxed at 60°-70° C. Acetone was added as necessary to keep the mixture in solution. After 6 hours the acetone solubles were pipetted off and dried at reduced pressure on a rotary evaporator. To remove the potassium carbonate, the dry acetone solubles were extracted with CHCl₃. The CHCl₃ solubles were separated on a Porasil A (Water's brand of high pressure ligand chromatography column) column using 1:1, CHCl₃:hexane. The chloroform/hexane extracts were evaporated to dryness, and the dried material was redissolved in hexane.

EXAMPLE III—PREPARATION OF DIISOPROPOXY MONORDEN

Diisopropoxy monorden was synthesized in the following manner Monorden, 200 mg. (0.0055 M.) was put in a solution of 8.3 ml. of dry acetone (distilled from potassium carbonate) and 0.7746 g (0.0055 M.) of anhydrous potassium carbonate was added, followed by 0.815 ml. (0.0082 M.) of 2-iodopropane. The mixture was refluxed for six hours at 56° and dry acetone was added as required to keep the mixture in solution. The acetone solubles were decanted. The acetone was removed at reduced pressure. The resulting solids were extracted with chloroform. Diisopropoxy monorden was isolated by crystallization from methanol. The physical characteristics of diisopropoxy monorden are set forth in Table I.

EXAMPLE IV—ACTIVITY AGAINST TUMOR CELLS

Tumorous human nasopharynx cells (also known as KB cells) were obtained. Following the procedure set forth in Cancer Chem. Rpts. 25, 52 (1962), the KB cells were cultured and inoculated with various levels of diethoxy monorden. It was established that the ED50 was 3.1 µg. Using the prescribed test procedure, levels of 4 µg./ml. or less indicate significant activity against tumor cells. Using the prescribed procedure, the ED50 values for di-n-propoxy monorden were 3.1 µg. and 3.9 µg. respectively. Dimethoxy monorden, a known compound, has an ED50 of 1.9 µg.

TABLE I

| | Diethoxy Monorden | Dipropoxy Monorden | Diisopropoxy Monorden |
|---|---|---|---|
| Melting Point | 142°-144° C. | 136°-319° C. | 140°-141° C. |
| UV Peak | 280 nm | 280 nm | 280 nm |
| IR Spectrum | 1750 | 1705 | 1705 |
| (Nujol) | 1690 | 1690 | 1688 |
| Peaks | 1670 | 1662 | 1662 |
| | 1610 | 1608 | 1605 |
| | 1595 | 1593 | 1590 |
| | 1460 | 1570 | 1568 |
| | 1440 | 1468 | 1468 |
| | 1425 | 1460 | 1460 |
| | 1400 | 1425 | 1422 |
| | 1388 | 1408 | 1403 |
| | 1380 | 1380 | 1379 |
| | 1355 | 1353 | 1368 |
| | 1330 | 1332 | 1350 |
| | 1305 | 1318 | 1330 |
| | 1290 | 1300 | 1315 |
| | 1280 | 1278 | 1297 |
| | 1260 | 1260 | 1272 |
| | 1250 | 1247 | 1258 |
| | 1200 | 1230 | 1240 |
| | 1180 | 1190 | 1277 |
| | 1152 | 1145 | 1190 |
| | 1140 | 1130 | 1140 |
| | 1120 | 1115 | 1125 |
| | 1112 | 1098 | 1110 |
| | 1078 | 1070 | 1092 |

TABLE I-continued

| Diethoxy Monorden | Dipropoxy Monorden | Diisopropoxy Monorden |
|---|---|---|
| 1032 | 1048 | 1068 |
| 950 | 1035 | 1042 |
| 930 | 1000 | 1030 |
| 870 | 985 | 1007 |
| 860 | 978 | 994 |
| 825 | 950 | 980 |
| 800 | 920 | 972 |
| 740 | 903 | 962 |
| 720 | 860 | 943 |
| | 830 | 912 |
| | 820 | 900 |
| | 745 | 890 |
| | 720 | 856 |
| | | 825 |
| | | 818 |
| | | 740 |
| | | 715 |

EXAMPLE V—NEMATOCIDE ACTIVITY

Suspensions of diethoxy monorden (DEM) in water were prepared by dissolving 2 milligrams of DEM in 200 µg of dimethyl sulfoxide (DMSO). Thereafter, the DMSO solution was dispersed rapidly into 1.8 ml of deionized water to provide a suspension of microcrystalline DEM. The DEM suspension was serially diluted in 3 fold steps and placed in standard 13×100 mm test tubes. Each tube contained 1 milliliter of a diluted DEM suspension. The levels of DEM employed (in mg/ml) were 0.0005, 0.0015, 0.0045, 0.0135, 0.0405, 0.1100 and 0.3300 and 1.0.

1 ml of water containing approximately 20 nematodes in suspension was placed in each tube and admixed with the DEM suspension. The nematodes had been previously collected from a soil sample by immersion of the soil in water followed by concentration of the nematodes by filtration. After 16 hours the viability of the nematodes was determined by microscopic examination. Absence of movement was taken as an indication of mortality. As a control, 1 ml of water with approximately 20 nematodes suspended therein was admixed with an aqueous solution of water containing 100 µg of DMSO—the highest level of DMSO present in the DEM suspension. After 16 hours the mortality level for the control was about 20%. Using the technique described by Reed and Muench (Am. J. Hygiene 27: 493–497, 1938) the DEM level resulting in 50% mortality (i.e., the "LC₅₀") after 16 hours was determined. For DEM the LC₅₀ was 0.2 mg/ml, clearly illustrating that DEM is an effective nematocide.

In a similar manner the LC₅₀ for di-isopropoxy monorden (DPM) was determined to be 0.8 mg/ml, which illustrates that DPM is an effective nematocide.

What is claimed is:

1. Dialkoxy monorden corresponding to the structural formula:

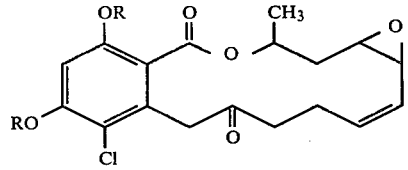

wherein R is an alkyl group having 3 carbon atoms, said R groups being the same and selected from the group consisting of propyl or isopropyl.

2. A compound as in claim 1 wherein the R group is propyl.

3. A compound as in claim 1 wherein the R group is isopropyl.

* * * * *